United States Patent
Riley et al.

(10) Patent No.: US 9,662,152 B2
(45) Date of Patent: May 30, 2017

(54) RESORBABLE HOLLOW DEVICES FOR IMPLANTATION AND DELIVERY OF THERAPEUTIC AGENTS

(75) Inventors: Susan Lynn Riley, San Diego, CA (US); Alexander R. Vaccaro, Gladwyne, PA (US); Joseph Tai, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 1408 days.

(21) Appl. No.: 12/424,140

(22) Filed: Apr. 15, 2009

(65) Prior Publication Data

US 2009/0259177 A1    Oct. 15, 2009

Related U.S. Application Data

(62) Division of application No. 11/357,837, filed on Feb. 16, 2006, now abandoned.
(Continued)

(51) Int. Cl.
*A61F 2/44* (2006.01)
*A61B 17/70* (2006.01)
(Continued)

(52) U.S. Cl.
CPC ......... *A61B 17/7097* (2013.01); *A61M 25/10* (2013.01); *A61M 25/1029* (2013.01); *A61M 31/002* (2013.01); *A61B 17/8833* (2013.01); *A61B 17/8855* (2013.01); *A61B 2017/00004* (2013.01); *A61B 2017/883* (2013.01); *A61B 2017/8813* (2013.01); *A61F 2/44* (2013.01); *A61F 2/4601* (2013.01); *A61F 2002/30062* (2013.01); *A61F 2002/30064* (2013.01); *A61M 2025/0057* (2013.01); *A61M 2025/105* (2013.01)

(58) Field of Classification Search
CPC ................. A61B 17/8858; A61B 17/8855
USPC ...... 623/17.11, 17.12, 17.16; 606/92–94, 62, 606/63, 67, 68
See application file for complete search history.

(56) References Cited

U.S. PATENT DOCUMENTS

| 3,173,418 A | 3/1965 | Baran |
| 3,297,033 A | 1/1967 | Schmitt et al. |

(Continued)

OTHER PUBLICATIONS

Wang et al. "A Novel Drug Carriers—Poly-/Pesudo-Polyamino Acids" J Biomed Eng., 1994-2010 China Academic Journal Electronic Publishing House, pp. 17-18.

*Primary Examiner* — Christian Sevilla
*Assistant Examiner* — Cheryl Miller
(74) *Attorney, Agent, or Firm* — Jeremy A. Smith; Bradley Arani Boult Cummings LLP

(57) ABSTRACT

A method of manufacturing a resorbable balloon designed to contain bone cement for vertebroplasty or kyphoplasty applications is described. The resorbable balloon can be inserted into a vertebral body following vertebral cavitation and filled with bone cement. The balloon remains in place in the vertebral body and resorbs over time. Methods and apparatus are also described for delivering therapeutic agents using collapsible, resorbable balloons. The balloons may be nested and filled with various therapeutic agents that are released over time at rates dependent upon structures and degradation rates of the balloons. Furthermore, the function of the hollow devices can encompass both encapsulation and therapeutic substance delivery roles simultaneously.

19 Claims, 6 Drawing Sheets

Related U.S. Application Data

(60) Provisional application No. 60/653,778, filed on Feb. 16, 2005, provisional application No. 60/672,839, filed on Apr. 18, 2005.

(51) Int. Cl.
*A61M 25/10* (2013.01)
*A61M 31/00* (2006.01)
*A61F 2/46* (2006.01)
*A61F 2/30* (2006.01)
*A61B 17/88* (2006.01)
*A61B 17/00* (2006.01)
*A61M 25/00* (2006.01)

(56) References Cited

U.S. PATENT DOCUMENTS

| | | |
|---|---|---|
| 3,901,232 A | 8/1975 | Michaels et al. |
| 3,944,064 A | 3/1976 | Bashaw et al. |
| 3,981,299 A | 9/1976 | Murray |
| 3,993,072 A | 11/1976 | Zaffaroni |
| 3,993,073 A | 11/1976 | Zaffaroni |
| 4,147,767 A | 4/1979 | Yapel, Jr. |
| 4,254,774 A | 3/1981 | Boretos |
| 4,305,392 A | 12/1981 | Chester |
| 4,349,530 A | 9/1982 | Royer |
| 4,417,576 A | 11/1983 | Baran |
| 4,518,383 A | 5/1985 | Evans |
| 4,693,243 A | 9/1987 | Buras |
| 4,906,244 A | 3/1990 | Pinchuk et al. |
| 4,925,677 A | 5/1990 | Feijen |
| 4,938,763 A | 7/1990 | Dunn et al. |
| 4,983,392 A | 1/1991 | Robinson |
| 4,994,033 A | 2/1991 | Shockey et al. |
| 5,041,090 A | 8/1991 | Scheglov et al. |
| 5,045,071 A | 9/1991 | McCormick et al. |
| 5,084,315 A | 1/1992 | Karimi et al. |
| 5,207,071 A | 5/1993 | Ozu et al. |
| 5,209,741 A | 5/1993 | Spaeth |
| 5,254,091 A | 10/1993 | Aliahmad et al. |
| 5,318,531 A | 6/1994 | Leone |
| 5,618,286 A | 4/1997 | Brinker |
| 5,685,716 A * | 11/1997 | Linkow .................. 433/173 |
| 5,780,044 A | 7/1998 | Yewey et al. |
| 5,800,421 A | 9/1998 | Lemelson |
| 5,868,705 A | 2/1999 | Bagaoisan et al. |
| 5,888,533 A | 3/1999 | Dunn |
| 5,904,934 A | 5/1999 | Maruyama et al. |
| 5,910,133 A | 6/1999 | Gould |
| 5,968,047 A | 10/1999 | Reed |
| 6,206,930 B1 * | 3/2001 | Burg .......................... A61F 2/02 623/23.64 |
| 6,544,221 B1 | 4/2003 | Kokish et al. |
| 6,599,462 B1 | 7/2003 | Miraki |
| 6,632,235 B2 * | 10/2003 | Weikel ................. A61B 17/025 606/192 |
| 6,645,422 B2 | 11/2003 | Jung, Jr. et al. |
| 6,656,488 B2 | 12/2003 | Yi et al. |
| 6,716,216 B1 | 4/2004 | Boucher et al. |
| 6,852,095 B1 * | 2/2005 | Ray .................... A61B 17/7097 604/93.01 |
| 7,226,481 B2 * | 6/2007 | Kuslich ...................... 623/17.11 |
| 7,618,451 B2 * | 11/2009 | Berez et al. .............. 623/14.12 |
| 7,717,956 B2 * | 5/2010 | Lang ..................... A61B 5/1077 623/14.12 |
| 7,938,835 B2 * | 5/2011 | Boucher ............ A61B 17/1631 606/92 |
| 8,562,634 B2 * | 10/2013 | Middleton ......... A61B 17/1615 606/170 |
| 2002/0068974 A1 * | 6/2002 | Kuslich .................. A61B 17/68 623/17.11 |
| 2002/0156482 A1 * | 10/2002 | Scribner ............ A61B 17/8855 606/92 |
| 2003/0139811 A1 | 7/2003 | Watson et al. |
| 2004/0220672 A1 * | 11/2004 | Shadduck .......... A61F 2/30965 623/17.16 |
| 2004/0230309 A1 * | 11/2004 | DiMauro et al. ......... 623/17.12 |
| 2005/0015060 A1 * | 1/2005 | Sweeney ...................... 604/264 |
| 2005/0021084 A1 | 1/2005 | Lu et al. |
| 2005/0146085 A1 | 7/2005 | Holman et al. |
| 2005/0209629 A1 * | 9/2005 | Kerr et al. .................... 606/192 |
| 2005/0261781 A1 * | 11/2005 | Sennett ............. A61B 17/7098 623/23.54 |
| 2006/0271061 A1 * | 11/2006 | Beyar et al. .................. 606/105 |
| 2006/0293750 A1 * | 12/2006 | Sherman .................. A61F 2/44 623/17.12 |
| 2007/0055300 A1 * | 3/2007 | Osorio .............. A61B 17/1604 606/192 |
| 2007/0093899 A1 * | 4/2007 | Dutoit .................. A61B 17/686 623/17.11 |
| 2007/0156251 A1 * | 7/2007 | Karmon .................. A61B 17/58 623/23.61 |
| 2008/0039849 A1 * | 2/2008 | Briest ................ A61B 17/8811 606/86 R |

* cited by examiner

RESORBABLE HOLLOW DEVICES FOR IMPLANTATION AND DELIVERY OF THERAPEUTIC AGENTS

CROSS-REFERENCE TO RELATED APPLICATIONS

This application is a divisional of U.S. application Ser. No. 11/357,837, filed Feb. 16, 2006 and entitled RESORBABLE HOLLOW DEVICES FOR IMPLANTATION AND DELIVERY OF THERAPEUTIC AGENTS, the entire contents of which are hereby incorporated by reference. U.S. application Ser. No. 11/357,837 claims the benefit of U.S. Provisional Application No. 60/653,778, filed Feb. 16, 2005, and U.S. Provisional Application No. 60/672,839, filed Apr. 18, 2005, the entire contents of both which are hereby incorporated by reference. This application relates to U.S. Pat. No. 7,090,668, filed Oct. 21, 2002 and entitled TIME-RELEASED SUBSTANCE DELIVERY DEVICE, the entire contents of which are incorporated herein by reference.

BACKGROUND OF THE INVENTION

1. Field of the Invention

The present invention relates generally to implants and, more particularly, to biomedical balloons and applications employing such balloons.

2. Description of Related Art

Balloon catheters have been employed in angioplasty applications for many years. A catheter having an inflatable balloon formed therein may be inserted into an artery percutaneously, and the balloon guided to a treatment area. The balloon may then be inflated in order to mitigate the effect of plaque deposits in, for example, a coronary artery. In some cases a balloon catheter is employed to implant a stent into an artery of a patient in order to decrease the likelihood of a recurrence of arterial blockage. Balloon catheters used in angioplasty are commonly removed from the patient after use as a result of, for example, typically being meant only to temporarily inflate the vessel or temporarily block the vessel for delivery of a stent or drugs. Additionally, removal of the balloon is typically necessary in order to attenuate complications that may arise pertaining, for example, to long-term effects which may stem from contact between a material of the balloon and the patient's tissue.

Balloon devices have found utility in biomedical areas other than cardiovascular applications. For example, balloons may be used in kyphoplasty applications wherein the effect of a vertebral fracture from osteoporosis is treated by inserting a balloon into a cavity formed in the fracture. Inflating the balloon may cause pieces of the fracture to return to a positions or orientations approximating those existing before for example a traumatic event that caused the fracture. Bone cement may then be inserted into the cavity in order to stabilize the bone fragments. In other vertebroplasty applications, bone cement may be inserted into, for example, cavities formed in weakened or fractured bones in order to provide enhanced strength and stability.

Unfortunately, cement extravasation can be a problem in these kyphoplasty and vertebroplasty situations. For instance, cement inserted into bone may extrude into surrounding tissues and nerves, causing pain and other complications. One way to prevent cement extravasation is to insert a balloon into the treatment cavity, fill the balloon with bone cement, and allow the cement to harden inside the balloon while the balloon remains in the body of the patient. Such a solution may not always be viable due for example to confounding factors such as situations wherein the presence of the balloon may prevent bonding between the bone cement and the bone tissue of interest. Consequently, gaps may form between an outer surface of the balloon and surrounding bone, introducing for example attendant risks of infection, bone loss, and pain.

A need thus exists in the prior art for a method of preventing cement extravasation in vertebroplasty and kyphoplasty applications. A further need exists for enabling bonding between bone cement and bone tissue following vertebroplasty and kyphoplasty treatments.

A medicinal substance can be administered to a patient systemically or locally. A systemically administered medicinal substance enters into the blood stream, travels throughout the body, and, preferentially, reaches the part of the patient's body in need of treatment at an effective dose before being degraded by metabolism and excreted. The systemic administration of medicinal substances can be achieved by oral application (e.g., syrups, tablets, capsules and the like), needle injection, transdermal delivery (e.g., a medicinal substance incorporated into a skin patch), and subdermal delivery (e.g., a medicinal substance formulation in a metabolizable matrix placed beneath the skin to release, for example, nicotine or birth control drugs). Systemically delivered medicinal substances can be inefficient when only a small amount of the administered dose reaches the site sought for therapeutic action. Moreover, with systemic delivery a medicinal substance can enter parts of the body where it can actually do harm or produce a noxious side effect.

Medicinal substances can be delivered locally by injection (e.g., injection of anesthetic into a patient's gums) or topically (e.g., creams, ointments, and sprays). Although the local delivery of medicinal substances can in some instances overcome problems of dilution and migration associated with systemic administration, multiple injections may be required to achieve or sustain a therapeutically effective dose over time. To avoid a need for multiple injections, a therapeutic agent may be delivered locally by way of a timed-released or controlled delivery type device. In many cases, timed-released devices are formed as a mixture or dispersion of the therapeutic agent in a degrading or non-degrading delivery material or vehicle. In some cases the therapeutic agent is destroyed, denatured, or looses its activity when combined with the delivery vehicle or material. In other cases, controlled delivery devices rely on diffusion of the therapeutic agent from the delivery material or vehicle, but the therapeutic agent may be too large to diffuse through a delivery material matrix of the controlled delivery device at a reasonable rate. In cases where the volume of the therapeutic time-released agent is large, an open procedure may be required to insert a relatively large therapeutic time-release device to the desired anatomical location. To avoid an open procedure for the delivery of a large volume of therapeutic agent, many small devices may be inserted, such as microspheres. The microspheres, however, may be difficult to retrieve if there is a complication. Even when local delivery of medicinal substances to a target site is possible, an important consideration still remains of maximizing the therapeutic effectiveness of the local drug delivery by controlling the proper dose and duration of the local delivery of the medicinal substance.

A need thus exists in the prior art for a delivery method or apparatus that can avoid undesirable activity losses of a therapeutic agent that may be associated with techniques that combine the therapeutic agent with a delivery material or vehicle. A further need exists for a method or apparatus that can avoid a requirement of diffusion of a therapeutic agent through a material of a delivery device. A still further need exists for methods or apparatus that may not require implantation of multitudes of small delivery devices and/or associated problems that may be presented of having to retrieve those small devices from an anatomical location upon the occurrence of complications, as well as methods or apparatus that may not require open surgical procedures for delivering large amounts of therapeutic agents.

SUMMARY OF THE INVENTION

The present invention provides a resorbable (e.g., bioresorbable, degradable, biodegradable, absorbable, bioabsorbable, erodible, bioerodible) balloon that can encapsulate cement in vertebroplasty and kyphoplasty applications until the cement has an opportunity to harden, thereby preventing incursion of the cement into soft tissue and nerves in a vicinity of bone being treated. The invention herein disclosed includes a method of forming a resorbable balloon comprising, according to an illustrative implementation, extruding resorbable tubing and cutting the tubing to desired lengths, thereby forming a plurality of tubes. A region of a tube is heated, and the tubing that forms the tube can be pulled along an axis of the tube, thereby thinning a wall of the tube at the heated region. Heated air is forced through a lumen of the tube while heating the region of the tube so that the tubing expands and forms a balloon in the heated region. An end of the tube is sealed by a thermal method or by gluing a resorbable plug into the lumen, and excess tubing beyond the sealed point is removed. According to an illustrative example, the resorbable balloon may be employed in a bone restoration procedure whereby a volume of bone is evacuated to form a cavity in the bone. A deflated resorbable balloon is inserted into the cavity, and the resorbable balloon is filled with bone cement, thereby inflating the balloon and filling the cavity. The resorbable balloon subsequently biodegrades to bring the bone cement into contact with bone within the cavity.

The present invention further provides apparatus and methods that may avoid problems associated with prior art methods of delivering therapeutic agents. Delivery methods and devices of various embodiments of the present invention may provide delivery of therapeutic agents while avoiding or attenuating problems associated with one or more of: combinations of the therapeutic agent with a delivery material or vehicle, diffusion through a material of the delivery device, implantation of multitudes of small delivery devices, and open surgical procedures. The invention herein disclosed thus can employ resorbable hollow devices which can be introduced into a desired anatomical location with, in many instances, a minimum of trauma. As an example, an implementation of a method according to the present invention can comprise a first collapsible resorbable hollow device, such as a resorbable balloon. A surgical procedure, which may be a laparoscopic procedure, may be performed to generate a cavity in a desired anatomical location of a body of a patient. The resorbable hollow device may be deflated, and subsequently inserted into the cavity. At least one therapeutic agent may be injected into the first collapsible resorbable hollow device. According to another implementation of the method, a second collapsible resorbable hollow device may be provided, and the second device may be inserted into the first collapsible resorbable hollow device. At least one therapeutic agent then may be injected into the second collapsible resorbable hollow device. Various therapeutic agents may be injected according to typical implementations of the present invention. For example, a therapeutic agent may comprise one or more of a natural organic substance, a synthetic organic substance, an inorganic substance, and combinations thereof.

Furthermore, the function of the hollow devices can encompass both encapsulation and therapeutic substance delivery roles simultaneously. An embodiment of the present invention may further comprise a collapsible resorbable balloon formed of resorbable material such as, for example, aliphatic polyesters, polycarbonates, polyoxaesters, polyorthoesters, polyanhydrides, polyphosphoesters, polyphosphazenes, polypropylene fumarates, polyamino acids, other polyamides, pseudopoly (amino acids), polyamidoesters, polyarylates, polyoxaesters containing amine groups, polyalkylene oxalate, polyhydroxybuyrate, polyhydroxyvalerate, resorbable polyurethanes, resorbable starches, resorbable silk, chitan or chitosan, and combinations (co- or multi-polymers or blends) of any of the above with or without, for example, nonresorbable polymers and/or natural substances.

While the apparatus and methods of the present invention have or may be described for the sake of grammatical fluidity with functional explanations, it is to be expressly understood that the claims, unless expressly formulated under 35 U.S.C. 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. 112 are to be accorded full statutory equivalents under 35 U.S.C. 112.

Any feature or combination of features described herein are included within the scope of the present invention provided that the features included in any such combination are not mutually inconsistent as will be apparent from the context, this specification, and the knowledge of one skilled in the art. For purposes of summarizing the present invention, certain aspects, advantages and novel features of the present invention are described herein. Of course, it is to be understood that not necessarily all such aspects, advantages or features will be embodied in any particular embodiment of the present invention. Additional advantages and aspects of the present invention will be apparent in the following detailed description and claims that follow.

DETAILED DESCRIPTION OF THE INVENTION

Figure 1:
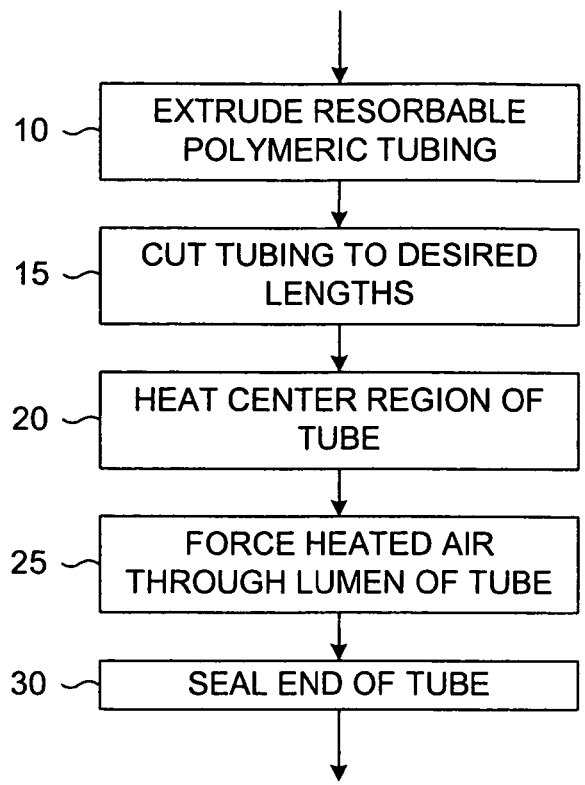
FIG. 1 is a flow diagram describing an implementation of a method of manufacturing a resorbable balloon.

Reference will now be made in detail to the presently preferred embodiments of the invention, examples of which are illustrated in the accompanying drawings. Wherever possible, the same or similar reference numbers may be used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, may be used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims. It is to be understood and appreciated that the process steps and structures described herein do not cover complete process flows for the manufacture of resorbable balloons and methods of administration of time-release therapeutic agents using resorbable balloons. The present invention may be practiced in conjunction with various techniques that may be conventionally used in the art, and only so much of the commonly practiced process steps are included herein as necessary to provide an understanding of the present invention. The present invention has applicability in the field of resorbable balloons or hollow devices in general. For illustrative purposes, however, the following description is presented in the context of a biodegradable (e.g., resorbable, bioresorbable, degradable, absorbable, bioabsorbable, erodible, or bioerodible) balloon for vertebroplasty and kyphoplasty applications and methods of manufacturing a biodegradable balloon, and in the context of biodegradable (e.g., resorbable, bioresorbable, degradable, absorbable, bioabsorbable, erodible, or bioerodible) balloons for delivering therapeutic agents over a distributed time span.

Figure 2A:
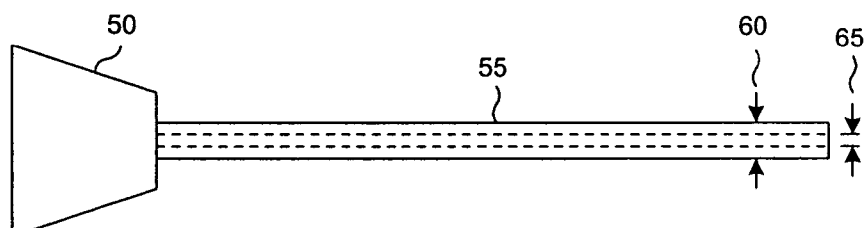
FIGS. 2a-2g are schematic diagrams illustrating results of applying steps of a method of manufacturing a resorbable balloon in accordance with an implementation of the present invention.
Figure 2B:

Referring more particularly to the drawings, FIG. 1 is a flow diagram describing an implementation of the inventive methods of manufacturing a resorbable (e.g., bioresorbable, degradable, biodegradable, absorbable, bioabsorbable, erodible, bioerodible) balloon. This implementation will be described with reference to FIGS. 2a-2g, which illustrate a representative sequence of performing steps of the methods. The illustrated embodiment of the described inventive methods comprises extruding resorbable tubing at step 10. The tubing extruded may comprise, for example, polymeric tubing in a representative embodiment. FIG. 2a illustrates an example of a mold 50 from which is extruded tubing 55. In typical embodiments, the tubing 55 may have a circular cross-section with an outer diameter 60 ranging, for example, from about 0.7 mm to about 15 mm and an inner diameter 65 that may range, for example, from about 0.5 mm to about 9 mm. That is, the tubing may exhibit a wall thickness of, for example, about 0.1 mm to about 3 mm in common embodiments. The tubing 55 may be cut into portions at step 15, wherein the portions may have various lengths according to varying intended applications. Tubes of resorbable material may thus be formed from the cutting performed at step 15. For example, a portion of tubing intended for use in angioplasty may range in length from, for example, about 50 mm to about 300 mm. A portion of tubing intended for use in vertebroplasty applications typically may be cut into lengths ranging in length from, for example, about 15 mm to about 100 mm. FIG. 2b illustrates two such tubes 70 and 75.

Figure 2C:
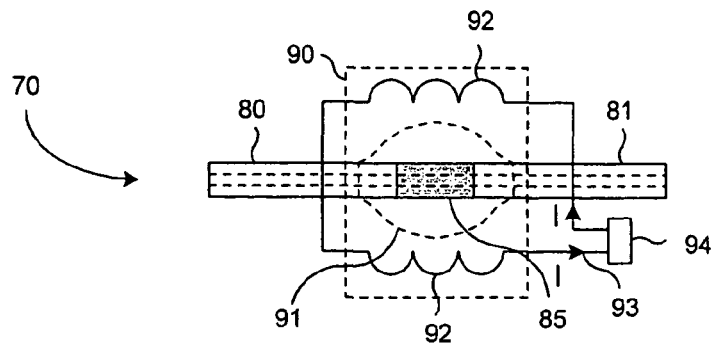

A portion of the tubing, e.g. tube 70 (FIG. 2b), then may be heated in a selected region at step 20. For example, a center region of the tube may be selected and heated. FIG. 2c illustrates a center region 85 of tube 70 being heated by an embodiment of an external heat source, which may comprise, for example, a mold formed, for example, of metal. In the illustrated embodiment, the mold comprises a heated mold 90. The heated mold 90 may comprise an internal chamber or cavity 91 having a shape and size equal or corresponding to, for example, one or more of a final balloon size and a final balloon shape. An exemplary embodiment of the heated mold 90 comprises electrical coils 92 through which may be passed a current 93 supplied from an electrical power source 94. Other internal heating means, and/or even external heating means, such as heating elements (e.g., flames) and/or electromagnetic energy (EM) emitting sources used for example with nonmetallic (e.g., non-EM blocking) molds, may be implemented in modified embodiments.

Regardless of the means used for providing heat, the heated mold 90 may in certain embodiments be configured to provide heat (and/or cooling), for example, in different amounts along one or more of: (a) at least one spatial dimension (e.g., along a longitudinal axis of the heated mold 90), and (b) a time dimension (e.g., at different points in time and/or for different durations). For example, when tubing is inserted into the heated mold 90 such that a longitudinal axis of the tubing is substantially aligned with a longitudinal axis of the heated mold 90, and when as in the illustrated embodiment tubing near the center of the cavity 91 is substantially further from walls of the heated mold 90 than tubing at ends of the cavity 91, greater amounts of heat energy may be provided near the center of the cavity 91 at certain points in time such as during the process of FIG. 2e.

Electrical coils in an illustrated embodiment of the heated mold 90 may be fabricated to have, for example, greater resistance in a center region of the heated mold 90 than at edges. Such an arrangement may provide greater $I^2R$ heating of metal near the center of the heated mold 90, wherein I represents current and R represents resistance. Thus, in an illustrative embodiment wherein the heated mold 90 comprises a block of metal housing electrical coils 92, certain parts of the heated portions of electrical coils 92 may be formed to comprise greater resistances (or other heating structures) to thereby provide varying amounts of heat at the heated portions of the electrical coils 92.

In an exemplary operation, tubing may be fed down a middle of the heated mold 90, and current 93 then turned on to raise a temperature of the heated mold 90. Typically, the heated mold 90 heats the tubing material to a temperature greater than a glass transition temperature, but below a melting temperature, of a material (e.g., a polymer) forming the tubing.

Figure 2D:
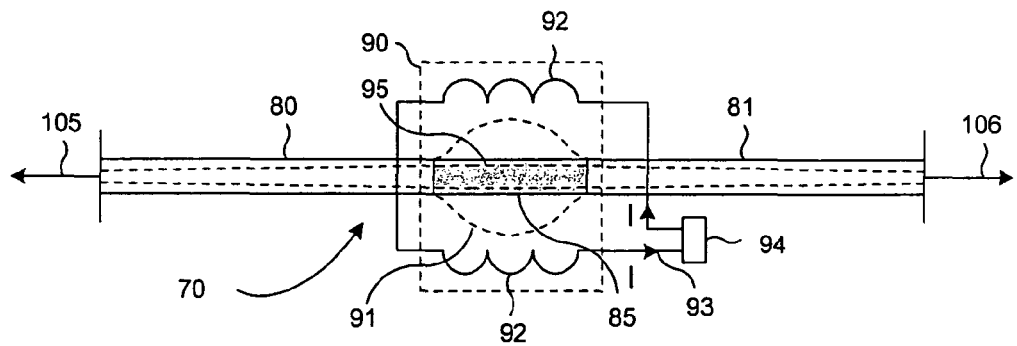

The heated center region 85, which is indicated in FIG. 2c with shading, is bounded by relatively unheated regions 80 and 81 of tubing on either side of the heated center region 85. According to an implementation of the methods of the present invention, after a condition has been met, such as an occurrence of one or more of a predetermined time period and a predetermined temperature, the material forming tube 70 may be pulled. In one embodiment, the material forming the tube 70 is pulled while being heated. When polymeric tubing is used, such pulling may accomplish one or more of strengthening and orienting a polymer or polymers of the tubing and causing the tubing wall to thin in the heated region. The pulling may increase the length of the heated center region of the tube 85 in a range of, for example, about 0 percent to about 1000 percent. The thickness of the thinned tubing wall 95 in the heated center region 85 may range from, for example, about 0.01 mm to about 0.5 mm when step 20 is concluded. FIG. 2d is a pictorial representation of an implementation of the heating/pulling operation just described. The pulling may be implemented, for example, by applying axial forces 105 and 106 to opposite ends of the tube 70.

Figure 2E:
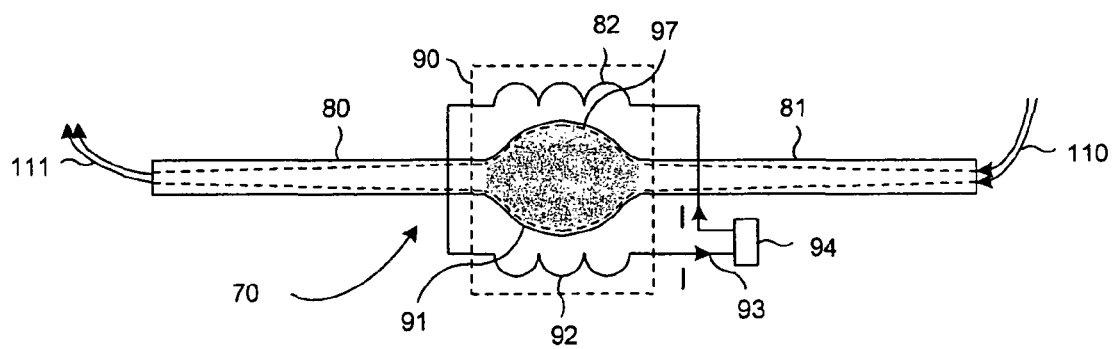
Figure 2F:
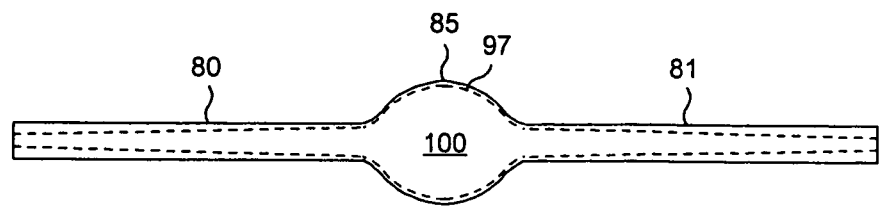

A balloon may be formed in the resorbable tube by forcing heated air through a lumen of the tube at step 25 while, in the illustrated embodiment, continuing to apply external heat, thereby causing the tubing to expand in the selected region. FIG. 2e illustrates the process. Fluid, such as air, which in the illustrated embodiment may comprise heated air 110, is directed, e.g., forced, into the tube 70. The directing of the fluid into the tube 70, e.g., into one or more ends of the tube 70, may result in one or more of further thinning of a wall 97 of the tube 70 and formation of a balloon 100 (FIG. 2f). In the illustrated embodiment, the directing of fluid into the tube 70 causes a pressure increase inside the tube 70. As presently embodied, the effect of the heat applied from the heated mold 90 and the heat of the heated air 110 can cause the tube 70 to expand in the center region 85, which action may result in thinning of the wall 97 of the tube 70 and formation of a balloon 100.

Figure 2G:
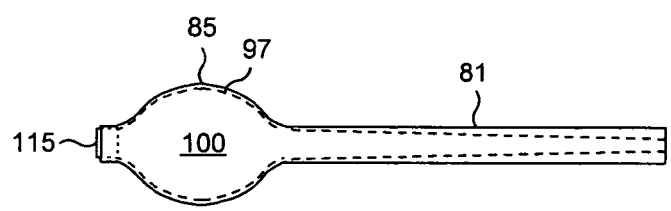

Exhaust air 111 may be directed out of the tube 70 via, for example, an end of the tube 70 that is opposite to an end through which the fluid is directed. According to this method, the thickness of the wall 97 of the balloon 100 may in the illustrated embodiment be reduced to a thickness of, for example, about 0.005 mm to about 0.1 mm. FIG. 2f illustrates an example of a balloon 100 formed according to the aforementioned steps after the heated mold 90 and a source of forced heated air 110 have been removed. In certain embodiments, the heated mold 90 may be partially or substantially completely (e.g., below a glass transition temperature) cooled before removal of the balloon 100 from the heated mold 90. Fabrication of the balloon 100 can then be completed by, for example, at least partially modifying, e.g., sealing, an end of the tube near the balloon 100 at step 30. For example, in FIG. 2g, a resorbable plug 115 is shown formed, e.g., integrally formed using heat, or affixed, e.g., adhered or glued, to an end of the balloon 100, thereby providing, for example, a seal at an end of the tube that is disposed in close proximity to the balloon 100. Excess tubing, corresponding for example to a relatively unheated region 80 (FIG. 2f), can be removed, e.g., cut off, beyond the sealed point as depicted in the embodiment of FIG. 2g. According to an alternative implementation of the method, one end of the tube can be modified, e.g., heat crimped, plugged, or otherwise closed, before the balloon 100 is formed, i.e., before the performance of step 20. Once formed, the balloon 100 may, for example, be deflated and configured, e.g., folded or twisted, to a cross-section of, for example, about the size of the relatively unheated region 81.

Figure 3:
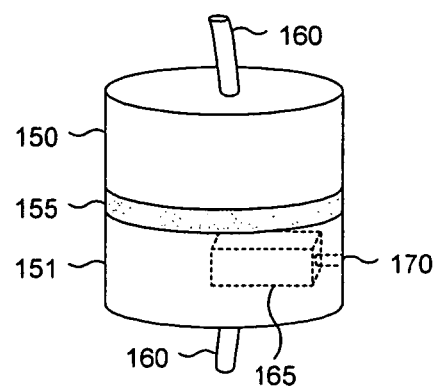
FIG. 3 is a simplified diagram illustrating a cavity in bone that may be filled with cement by employing a resorbable balloon according to the present invention.

FIG. 3 is a simplified diagram illustrating a cavity in bone that may be filled with cement by employing a resorbable balloon in accordance with an aspect of the present invention. Bone such as vertebral bodies of the spine in a patient is represented in FIG. 3 by two cylinders 150 and 151 separated by a cushioning disk 155. A representation 160 of a spinal cord that passes through the vertebrae 150 and 151 and the disk 155 also is shown. A cavity 165 has been formed in vertebra 151 representing a cavity that may be formed in, for example, an injured or osteoporotic spine. An access passageway 170 formed in the vertebra 151 provides a means for access to the cavity 165. In at least one implementation, a diameter, e.g., a maximum diameter, of the access passageway 170 is less than a diameter, e.g., a maximum diameter, of the cavity 165. In other embodiments, however, a diameter of the access passageway 170 may be about equal to or greater than a corresponding, e.g., measured in the same or similar direction, diameter of the cavity 165.

In accordance with an aspect of the present invention, tubing comprising a resorbable balloon that is similar to the balloon 100 illustrated in FIG. 2g can be formed as described herein. A property, e.g., dimension such as diameter, of the tubing is chosen such that the tubing and the balloon in its deflated state are capable of being inserted through access passageway 170 and into the cavity 165. For instance, properties of the tubing and/or balloon may be selected such that the tubing and balloon may be folded to facilitate insertion through the access passageway 170. According to at least one implementation, the tubing and balloon are maneuvered through the access passageway 170 and into the cavity 165 using a catheter. Once inside the cavity 170, a material such as bone cement may be inserted, e.g., injected, into a lumen of the tube. In implementations comprising a catheter, the material may be delivered directly into the balloon via the catheter, wherein, for example, the material does not contact internal surfaces of the tubing during transit to the balloon. Other implementations may comprise, for example, delivery of the material into the balloon via the tubing itself, wherein, for example, the material contacts the tubing during transit to the balloon. In one embodiment, insertion of the material at least partially fills, e.g., inflates, the balloon.

According to an illustrated embodiment, one or more of a size and a shape of the balloon can be chosen such that the balloon is capable of conforming to sides of the cavity 165 when, for example, the balloon is inflated. In implementations utilizing a catheter, once the material has been delivered into the balloon and, for example, the balloon has expanded to substantially fill the cavity 165, the catheter may be removed from the resorbable balloon, whereby the balloon with the material remains inside the cavity. Thus, a resorbable balloon can be positioned within a cavity and filled with a material to accomplish expansion and conformance of the balloon to interior dimensions of the cavity.

As presently embodied, with a passage of time at least a part of the balloon degrades, causing the material within the balloon to be delivered into contact with a corresponding interior surface or surfaces of or within the cavity. In particular implementations, the resorbable balloon is not removed and resorbs substantially completely within the cavity. Resorption of the balloon can be engineered to occur, for example, after the material has contacted and at least partially reacted, e.g., bonded, with interior surfaces within the cavity. In exemplary embodiments comprising a cavity formed in bone, material comprising bone cement can be positioned within a resorbable, expandable balloon, combined, in some implementations, with one or more of an antibiotic, analgesic, growth factor (such as Bone Morphogenetic Protein), or a combination thereof, to contact interior surfaces of a cavity formed within bone, thereby permitting one or more of reacting, hardening, and bonding to occur between the material and the bone upon resorption of the balloon. Consequently, risks of one or more of infection and pain can be attenuated or eliminated.

Figure 4:
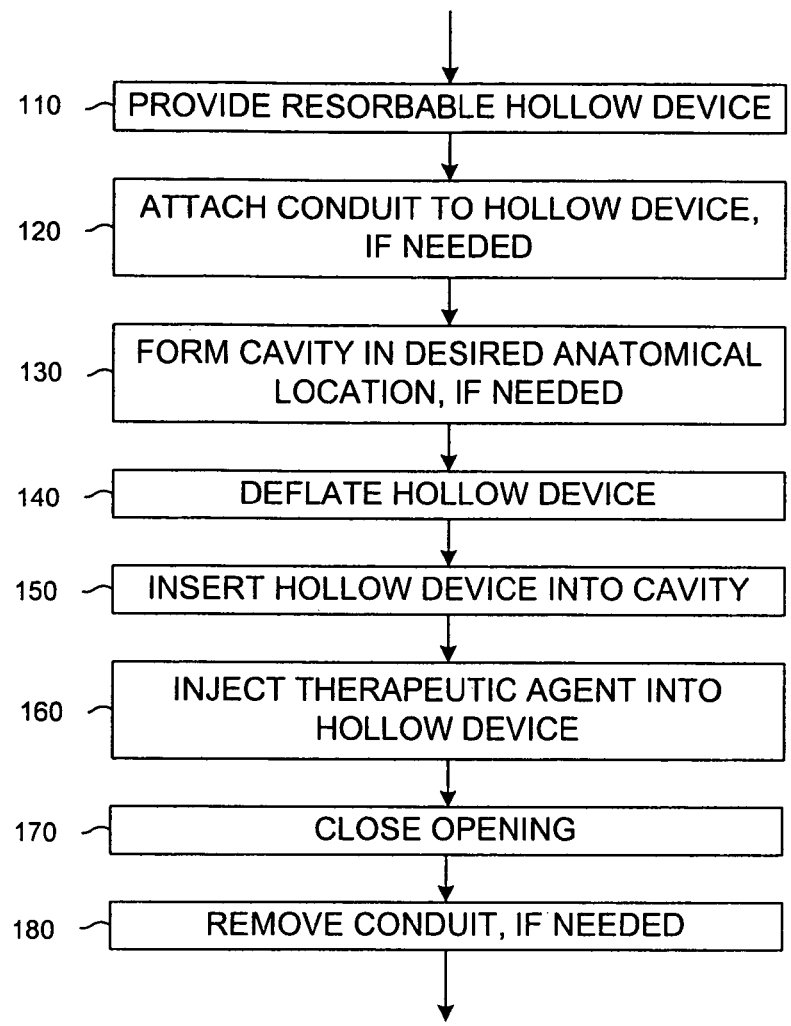
FIG. 4 is a flow diagram describing an implementation of a method of delivering a therapy or therapeutic agent employing collapsible resorbable hollow devices.

FIG. 4 is a flow diagram describing an implementation of a method of performing therapy employing collapsible resorbable hollow devices. According to the implementation described in the figure, a collapsible, resorbable hollow device, cavity, or balloon is provided at step 110. A method of fabricating collapsible, resorbable hollow devices of a type appropriate to the implementation is described in U.S. Provisional Application No. 60/653,778, the entire contents of which are hereby incorporated by reference. Although step 110 of the implementation comprises providing a single collapsible, resorbable hollow device, other implementations may comprise providing two or more collapsible, resorbable hollow devices.

Figure 5:
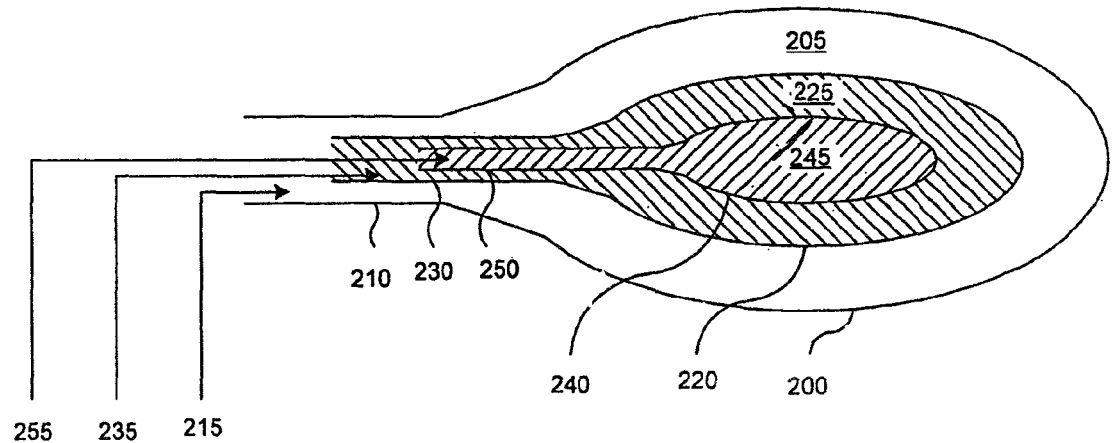
FIG. 5 is a pictorial diagram illustrating three resorbable hollow devices according to an example of the present invention.

In other implementations, the collapsible, resorbable hollow devices may be nested as illustrated, for example, in FIG. 5. The collapsible, resorbable hollow devices may be designed to deliver or release at least one therapeutic agent. As part of the fabrication of the hollow device, a conduit or tube may be attached, if needed (e.g., suitable or desired), to an opening of the device at step 120 of the implementation. According to another embodiment, the conduit may be formed as a continuous part of the hollow device. The conduit (see, e.g., FIG. 5) may facilitate loading of the hollow device with at least one therapeutic agent. Additionally, the conduit may aid in positional manipulation of the hollow device.

A surgical procedure, which may be a laparoscopic procedure, may be performed, if needed (e.g., suitable or desired), at step 130 to identify a cavity in an anatomical location. As presently embodied, a cavity in a desired anatomical location may also be formed. For example, a cavity may be formed in soft tissue using a tissue expander. Alternatively, a cavity may be formed in a collapsed vertebra of the spine of a patient, wherein therapy is to be performed. As another example, a cavity may be identified in the abdomen or other part of the body of a patient near an abscess requiring antibiotic therapy. Once the cavity is formed or identified, the hollow device may, to the extent inflated, be at least partially deflated at step 140, and the hollow device inserted into the cavity at step 150. The attached conduit, for example, may facilitate insertion and positional manipulation of the hollow device. A therapeutic agent, such as an antibiotic, may be injected into the hollow device at step 160, thereby inflating the hollow device. Alternatively, the hollow device may be inflated before the therapeutic agent is injected. According to other implementations, the inflating may be performed by altering an internal or external physical or chemical environment of the device when the device is in living tissue. The conduit may also be used to transfer the therapeutic agent into the hollow device. The opening may be closed at step 170 after which the conduit may then be removed, if needed (e.g., suitable or desired), from the hollow device at step 180. According to another implementation, the opening is closed after removal of the conduit. In yet another implementation, the opening is closed during removal of the conduit. In yet another implementation, the opening is not closed, as may occur when the device is used to transfer gelling or polymerizing substances as therapeutic agents.

The therapeutic agent may be delivered in a time-released manner according to specific properties of the hollow device. For example, the device may be fabricated with varying thicknesses or with relatively small perforations or holes, sizes of which may be adjusted to achieve a desired rate of delivery of the therapeutic agent. In other examples, more than one collapsible, resorbable hollow device may be employed. A second collapsible device may be inserted inside a first collapsible hollow device, the first device then being injected with one or more or a combination of therapeutic agents. The second collapsible device then may be inflated, and yet another therapeutic agent or combination thereof may be injected into the second device. This process may be continued by nesting a plurality of collapsible, resorbable hollow devices in a manner that should be clear to one skilled in the art from the disclosure provided herein. When a plurality of hollow devices or balloons is employed, openings of the hollow devices may be closed separately either before, after, or during removal of conduits associated with each device. In some instances, the openings may be closed together. In still other examples, nested hollow devices may be made with differing materials or geometry (shapes). Alternatively, space, or lack of space, between the devices can be used to achieve desired patterns of release of therapeutic material.

FIG. 5 is a pictorial diagram illustrating an embodiment comprising a plurality of nested hollow devices according to the present invention. Although only three such devices are illustrated in the figure, one skilled in the art will understand that more or fewer hollow devices may be employed so that a description of three devices is by way of example and not by way of limitation. In the illustrated embodiment, a first collapsible, resorbable hollow device 200 is inflated and fully or partially filled with a first therapeutic agent 205. That is, the first collapsible, resorbable hollow device 200 may, in some instances, be partially filled in order to leave room for insertion of subsequent hollow devices. As already noted, the first therapeutic agent, as well as below-referenced additional therapeutic agents, may comprise one or more or a combination of individual therapeutic agents. The first therapeutic agent 205 may be loaded into the first hollow device 200 through a first tube or first conduit 210 formed as part of the first hollow device. Loading of first therapeutic agent 205 is noted on the diagram by reference numeral 215. A second collapsible, resorbable hollow device 220 may be inserted using second conduit 230 in deflated form, and the device 220 then may be partially or fully inflated. According to an exemplary embodiment, loading the second hollow device 220 with a second therapeutic material 225 through second conduit 230 as denoted by reference numeral 235 may serve to inflate the second hollow device 220, thereby displacing or redistributing a portion of the first therapeutic agent 205 already loaded. Continuing, a third collapsible, resorbable hollow device 240 may likewise be inserted into the second device 220 and loaded using third conduit 250 as indicated by reference numeral 255. Once in place, respective first, second, and third conduits 210, 230, and 250 may be removed using any of several methods well-known in the art, leaving, for example, seal 260 in place as illustrated in FIG. 6.

Figure 6:
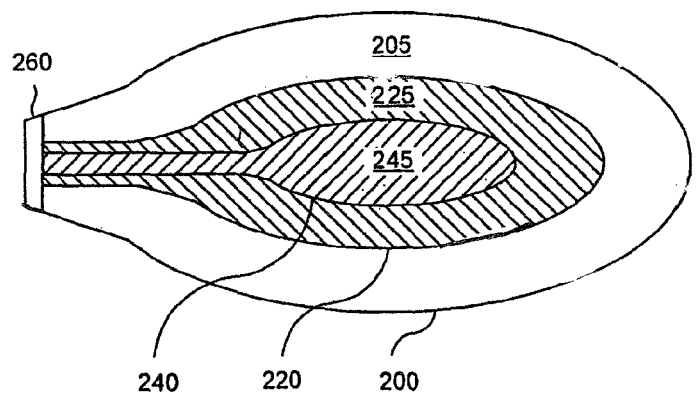
FIG. 6 is a pictorial diagram illustrating the three resorbable hollow devices of FIG. 5 with openings sealed or closed in some way, if needed, and conduits removed.

The collapsible, resorbable hollow devices 200, 220, and 240 illustrated in FIGS. 5 and 6 may be formed of various materials. For example, a representative hollow device can be made with a resorbable synthetic polymer including by way of example, and not by way of limitation, one or more of aliphatic polyesters (e.g., poly L-lactide, poly D-lactide, polyglycolide, poly epsilon-caprolactone, and the like), polycarbonates (e.g., polytrimethylene carbonate, tyrosine derived polycarbonates, and polyiminocarbonates), polyoxaesters (e.g., polyp-dioxanone), polyorthoesters, polyanhydrides, polyphosphoesters, polyphosphazenes, polypropylene fumarates, polyamides (e.g., polyaminoacids), pseudopoly(amino acids), polyamidoesters, polyarylates, polyoxaesters containing amine groups, polyalkylene oxalate, polyhydroxybuyrate, polyhydroxyvalerate, resorbable polyurethanes, resorbable starches, resorbable silk, chitan or chitosan and combinations (co- or multi-polymers or blends) of any of the above with or without, for example, nonresorbable polymers (e.g., polyethylene oxide, and polyvinyl alcohol) and/or natural substances, and other combinations thereof. Depending at least in part upon fabrication material, hollow devices may be made to resorb (e.g., bioresorb, degrade, biodegrade, absorb, bioabsorb, erode, or bioerode) over time periods ranging from a few days to a number of years according to a desired release rate of a therapeutic agent.

Therapeutic agents may have the consistency of, for example, one or more of a liquid, gel, powder, small granules, spheres or chips, a polymerizable substance, and combinations thereof, and likewise, may be chosen from a variety of possibilities. For example, a natural organic substance can be or include one or more of living biological agents (e.g., cells), proteins (e.g., growth factors such as Bone Morphogenetic Protein, and the like), other natural polymers (e.g., collagen, gelatin, fibrin, hyaluronic acid, polysaccharides, elastin, cellulose, polynucleotides), other biological materials, and the like. Combinations of these and similar materials also may be used. In other instances, the therapeutic agent may comprise a synthetic organic substance, such as, for example, one or more of a drug, antibiotic, steroid, glycerol, polymer (e.g., polyester, silicone, polyethylene oxide, polypropylene fumarate, pluronics, polyhydroxymethacrylate, or polymethylmethacrylate), and the like, and combinations thereof. In still other cases, the therapeutic agent may comprise an inorganic substance, such as, for example, one or more of calcium phosphate (e.g., beta-tricalcium phosphate or hydroxapatite), allograft bone, other ceramics or metals, and combinations thereof. The therapeutic agents may be made in combinations from any of the above components or groups or other suitable carrier(s), examples of which may include cells loaded in a pluronic gel or growth factors and antibiotics mixed with an inorganic substance.

Figure 7:
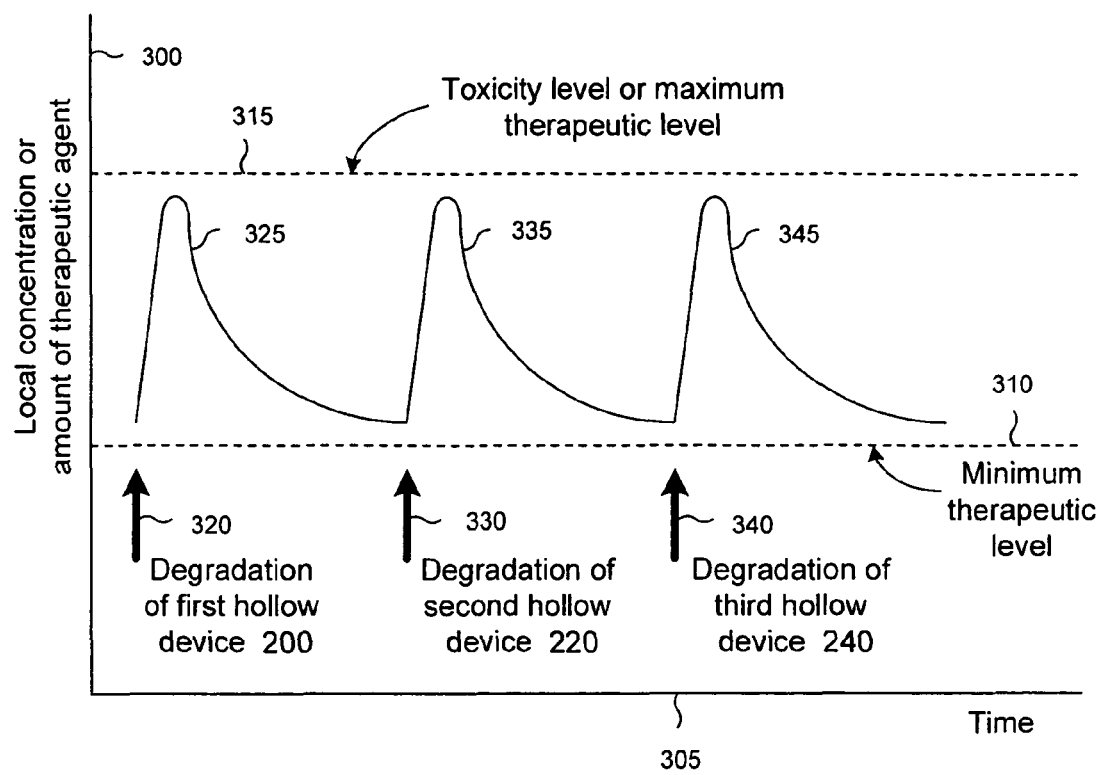
FIG. 7 is a graphical chart illustrating timed-release delivery of therapeutic agents.

FIG. 7 is a chart illustrating in graphical form an example of how release of a therapeutic agent may be controlled through use of resorbable hollow devices in a repeat action dosage form. The chart illustrates a variation of local concentration or amount of a therapeutic agent on a vertical axis 300 during a time period drawn on a horizontal axis 305. The amount of therapeutic agent to be released normally is to be kept between a minimum therapeutic level 310 and a maximum therapeutic level 315. The maximum therapeutic level 315 may correspond as well to a toxicity level. The chart of FIG. 7 is keyed to the first, second, and third resorbable hollow devices 200, 220, and 240 depicted in FIGS. 5 and 6. In the example illustrated, first hollow device 200 becomes resorbed (i.e. degrades) at a first time 320 releasing a first wave 325 of the therapeutic agent. As time increases to the right, the level of therapeutic agent represented by first wave 325 decreases. At a second time 330, second hollow device 220 degrades releasing a second wave 335 of the therapeutic agent. Similarly, third hollow device 240 degrades at a third time 340 releasing a third wave 345 of the therapeutic agent. The actual elapsed time between degradation of the first, second, and third hollow devices 200, 220, and 240 may be controlled, as noted above, by choosing materials from which the devices are fabricated, and/or constructions (e.g., designing the devices with small holes or perforations), or the like. The time intervals between times 320, 330, and 340 may be the same or different. First, second, and third therapeutic agents 205, 225, and 245 (FIGS. 5 and 6), likewise, may be the same or different in different embodiments of the present invention.

For example, first, second, and third resorbable hollow devices 200, 220, and 240 could be designed, respectively, to degrade slowly, at a medium rate, and quickly, and to therefore release, again respectively, first, second, and third therapeutic agents 205, 225 and 245 after, still again, respectively, a long, medium, and short period of time. In one embodiment, first, second, and third therapeutic agents 205, 225, and 245 are different or comprise different combinations or concentrations of therapeutic agents. In another embodiment, first, second, and third therapeutic agents 205, 225, and 245 are the same agent, and the different degradation rates of the hollow devices 200, 220, and 240 serve to release the agent over a relatively long period of time, and/or possibly in short bursts, but, for example, above the therapeutic minimum level 310 and below the maximum therapeutic level or below the toxicity level 315. In yet another embodiment, a hollow device, such as second hollow device 220, can be made to have perforations or holes, or no perforations, and may be covered or layered with another hollow device, such as first hollow device 200 having a faster degradation rate. This arrangement may allow release of the second therapeutic agent 225 through the holes of the second hollow device 220 (i.e., the more slowly degrading device) when the first hollow device 200 (i.e., the more rapidly degrading device) degrades.

In view of the foregoing, it will be understood by those skilled in the art that the methods of the present invention can facilitate formation of resorbable balloons and control of time-release therapeutic agents using collapsible, resorbable hollow devices or balloons. The above-described embodiments have been provided by way of example, and the present invention is not limited to the described examples. Multiple variations and modifications to the disclosed embodiments will occur, to the extent not mutually exclusive, to those skilled in the art upon consideration of the foregoing description. For example, the resorbable balloon may be used for other implanting applications such as a bariatric balloon, breast augmentation balloon, etc. Furthermore, modifications to the above-described manufacturing techniques may include, for example, a continuous extrusion and balloon forming method, and alternative implementations of such techniques may include, for example, extrusion of tubing with one closed end resembling the shape of, for example, a blow molding parison. Other combinations, omissions, substitutions and modifications will be apparent to the skilled artisan in view of the disclosure herein. Accordingly, the present invention is not intended to be limited by the disclosed embodiments, but is to be defined by reference to the appended claims.

What is claimed is:

1. A method of restoring bone, comprising:
   identifying a cavity within an interior of a vertebra bone;
   inserting a first resorbable balloon through an access passageway to the interior of the vertebra bone and into the cavity;
   inserting a second resorbable balloon through the access passageway to the interior of the vertebra bone and into the cavity such that the second resorbable balloon is nested within the first resorbable balloon, wherein the inserting of the second resorbable balloon occurs after the inserting of the first resorbable balloon;

injecting a therapeutic agent into at least one of the first and second resorbable balloons;

wherein the first and second resorbable balloons remain in the cavity for an amount of time until the first and second resorbable balloons degrade, thereby allowing the therapeutic agent to be delivered into contact with an interior surface of the cavity.

2. The method of claim 1, wherein the one of the first and second resorbable balloons includes a conduit.

3. The method of claim 1, wherein the therapeutic agent is injected into one of the first and second resorbable balloons through a catheter.

4. The method of claim 1, wherein the therapeutic agent is bone cement.

5. The method of claim 1, wherein the therapeutic agent is bone cement mixed with at least one of antibiotic, analgesic, and growth factor.

6. A method of restoring bone, comprising:

identifying a cavity within an interior of a vertebra bone;

inserting a plurality of resorbable balloons through an access passageway to the interior of the vertebra bone and into the cavity, wherein the plurality of resorbable balloons include a first resorbable balloon and a second resorbable balloon, and further wherein the first resorbable balloon is nested within the second resorbable balloon;

injecting at least one therapeutic agent into at least one of the first and second resorbable balloons, wherein the at least one therapeutic agent includes bone cement mixed with at least one of antibiotic, analgesic, and growth factor;

wherein the first and second resorbable balloons remain in the cavity for an amount of time until the first and second resorbable balloons degrade, thereby allowing the at least one therapeutic agent to be delivered into contact with an interior surface of the cavity, and wherein the at least one of the first and second resorbable balloons includes a conduit as a continuous part.

7. A method of restoring bone, comprising:

identifying a cavity within an interior of a vertebra bone;

inserting a plurality of resorbable balloons through an access passageway to the interior of the vertebra bone and into the cavity, wherein the plurality of resorbable balloons include a first resorbable balloon and a second resorbable balloon, and further wherein the first resorbable balloon is nested within the second resorbable balloon;

injecting at least one therapeutic agent into at least one of the first and second resorbable balloons, wherein the at least one therapeutic agent includes bone cement mixed with at least one of antibiotic, analgesic, and growth factor;

wherein each of the first and second resorbable balloons degrades at a different time and remains in the cavity until it degrades, thereby allowing the at least one therapeutic agent to be delivered into contact with an interior surface of the cavity.

8. The method of claim 7, wherein the at least one of the first and second resorbable balloons includes a conduit.

9. The method of claim 8, wherein the conduit is attached to an opening in at least one of the first and second resorbable balloons.

10. The method of claim 9, wherein the opening in the at least one of the first and second resorbable balloons is closed after the at least one therapeutic agent is injected into the at least one of the first and second resorbable balloons.

11. The method of claim 8, wherein the conduit is formed as a continuous part of the at least one of the first and second resorbable balloons.

12. The method of claim 8, wherein an opening in the at least one of the first and second resorbable balloons is closed after the at least one therapeutic agent is injected into the balloon with the conduit.

13. The method of claim 7, wherein at least one of the first and second resorbable balloons degrades substantially completely.

14. The method of claim 7, wherein at least one of the first and second resorbable balloons is inserted through an access passageway to the interior of the vertebra bone into the cavity using a catheter.

15. The method of claim 14, wherein the at least one therapeutic agent is injected into at least one of the first and second resorbable balloons through the catheter.

16. The method of claim 7, wherein the at least one therapeutic agent is injected into at least one of the first and second resorbable balloons through a catheter.

17. The method of claim 7, wherein injecting the at least one therapeutic agent into at least one of the first and second resorbable balloons at least partially inflates the at least one resorbable balloon.

18. The method of claim 7, wherein at least one of the first and second resorbable balloons is at least partially deflated before the at least one therapeutic agent is injected into the at least one resorbable balloon.

19. The method of claim 7, wherein at least one of the first and second resorbable balloons includes one of varying thickness or small perforations in an exterior surface adjusted to achieve a desired rate of delivery of the at least one therapeutic agent.

* * * * *